(12) United States Patent
Hastings

(10) Patent No.: US 10,582,834 B2
(45) Date of Patent: Mar. 10, 2020

(54) LOCATABLE EXPANDABLE WORKING CHANNEL AND METHOD

(75) Inventor: Paige B. Hastings, Bloomington, MN (US)

(73) Assignee: COVIDIEN LP, Mansfield, MA (US)

( * ) Notice: Subject to any disclaimer, the term of this patent is extended or adjusted under 35 U.S.C. 154(b) by 813 days.

(21) Appl. No.: 13/161,410

(22) Filed: Jun. 15, 2011

(65) Prior Publication Data

US 2012/0022325 A1 Jan. 26, 2012

Related U.S. Application Data

(60) Provisional application No. 61/355,115, filed on Jun. 15, 2010.

(51) Int. Cl.
*A61B 1/00* (2006.01)
*A61B 1/018* (2006.01)
(Continued)

(52) U.S. Cl.
CPC ........ *A61B 1/00087* (2013.01); *A61B 1/0051* (2013.01); *A61B 1/0057* (2013.01); *A61B 1/018* (2013.01); *A61B 1/2676* (2013.01); *A61B 5/065* (2013.01); *A61B 5/6852* (2013.01); *A61B 17/00234* (2013.01); *A61B 1/00135* (2013.01);
(Continued)

(58) Field of Classification Search
CPC ... A61B 1/0055; A61B 1/00071; A61B 1/018; A61B 1/005; A61B 1/00073; A61B 1/00135; A61B 1/00082; A61B 1/00078; A61B 1/00087; A61B 1/00131; A61B 1/00142; A61B 1/00154; A61B 1/008; A61B 1/01; A61B 1/012; A61B 1/0125; A61B 1/267; A61B 1/2673; A61B 1/2676; A61B 1/273; A61B 1/2733; A61B 1/2736; A61B 1/31; A61B 17/00234; A61B 2017/00292; A61B 2017/00296;
(Continued)

(56) References Cited

U.S. PATENT DOCUMENTS 1,576,781 A 3/1926 Phillips
1,735,726 A 11/1929 Bornhardt
(Continued)

FOREIGN PATENT DOCUMENTS

CA 964149 3/1975
DE 3042343 A1 6/1982
(Continued)

OTHER PUBLICATIONS

United States Patent and Trademark Office, Final Office Action dated May 1, 2012 in U.S. Appl. No. 12/476,976, 6 pages.
(Continued)

*Primary Examiner* — Ryan N Henderson

(57) ABSTRACT

A method and device is provided for accessing a target location within a branched network. The device may be passed through the working channel of a standard endoscope and includes a three-dimensional location sensor at its distal tip and an expandable extended working channel. The device has a very thin body proximal of the distal sensor such that, once the sensor is extended outside of the working channel of the endoscope, nearly all of the working channel may be used to pass tools through the extended working channel of the device.

20 Claims, 1 Drawing Sheet

(51) Int. Cl.
  *A61B 5/00* (2006.01)
  *A61B 1/267* (2006.01)
  *A61B 5/06* (2006.01)
  *A61B 1/005* (2006.01)
  *A61B 17/00* (2006.01)

(52) U.S. Cl.
  CPC .............. *A61B 2017/003* (2013.01); *A61B 2017/00292* (2013.01); *A61B 2017/00296* (2013.01); *A61B 2017/00318* (2013.01)

(58) Field of Classification Search
  CPC ... A61B 2017/003; A61B 2017/00318; A61M 25/0032; A61M 2025/0035
  USPC ........ 600/103–107, 109–110, 114–116, 139; 604/57; 606/106
  See application file for complete search history.

(56) References Cited

U.S. PATENT DOCUMENTS

| | | |
|---|---|---|
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kahne et al. |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,403,321 A | 9/1983 | DiMarco |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,447,224 A | 5/1984 | Decant, Jr. et al. |
| 4,447,462 A | 5/1984 | Tafuri et al. |
| 4,485,815 A | 12/1984 | Amplatz |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,586,491 A | 5/1986 | Carpenter |
| 4,607,619 A | 8/1986 | Seike et al. |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Budermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,669,172 A | 6/1987 | Petruzzi |
| 4,673,352 A | 6/1987 | Hansen |
| 4,688,037 A | 8/1987 | Krieg |
| 4,701,049 A | 10/1987 | Beckmann et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,679 A | 3/1989 | Shimonaka et al. |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |

(56) References Cited

U.S. PATENT DOCUMENTS

| | | |
|---|---|---|
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,951,677 A | 8/1990 | Crowley et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 4,994,069 A | 2/1991 | Ritchart et al. |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,021,888 A | 6/1991 | Yuu et al. |
| 5,025,778 A * | 6/1991 | Silverstein ............ A61B 1/0008 600/104 |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,186 A | 10/1991 | Yamamoto et al. |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,104,393 A | 4/1992 | Isner et al. |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vilkomerson et al. |
| 5,171,245 A | 12/1992 | Cezana |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,217,001 A * | 6/1993 | Nakao ............... A61B 1/00135 24/DIG. 50 |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,622 A | 7/1993 | Brossoit |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,301,061 A | 4/1994 | Nakada et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,341,807 A | 8/1994 | Nardella |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,380,302 A | 1/1995 | Orth |
| 5,383,454 A | 1/1995 | Bucholz |
| 5,383,852 A | 1/1995 | Stevens-Wright |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |

(56) References Cited

U.S. PATENT DOCUMENTS

| | | |
|---|---|---|
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,474,075 A | 12/1995 | Goldberg et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,489,256 A | 2/1996 | Adair |
| 5,490,196 A | 2/1996 | Rudich et al. |
| 5,494,034 A | 2/1996 | Schlondorff et al. |
| 5,503,416 A | 4/1996 | Aoki et al. |
| 5,503,616 A * | 4/1996 | Jones ............... A61B 1/00135 600/121 |
| 5,506,102 A | 4/1996 | McDonnell |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,522,815 A | 6/1996 | Durgin, Jr. et al. |
| 5,531,227 A | 7/1996 | Schneider |
| 5,531,520 A | 7/1996 | Grimson et al. |
| 5,531,686 A | 7/1996 | Lundquist et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,555,883 A | 9/1996 | Avitall |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-haim |
| 5,571,083 A | 11/1996 | Lemelson |
| 5,572,999 A | 11/1996 | Funda et al. |
| 5,573,493 A | 11/1996 | Sauer et al. |
| 5,573,533 A | 11/1996 | Strul |
| 5,575,794 A | 11/1996 | Walus et al. |
| 5,575,798 A | 11/1996 | Koutrouvelis |
| 5,577,991 A | 11/1996 | Akui et al. |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,175 A | 7/1997 | Adair |
| 5,643,268 A | 7/1997 | Vilsmeier et al. |
| 5,645,065 A | 7/1997 | Shapiro et al. |
| 5,646,524 A | 7/1997 | Gilboa |
| 5,647,361 A | 7/1997 | Damadian |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,696,500 A | 12/1997 | Diem |
| 5,697,377 A | 12/1997 | Wittkampf |
| 5,702,406 A | 12/1997 | Vilsmeier et al. |
| 5,711,299 A | 1/1998 | Manwaring et al. |
| 5,713,853 A | 2/1998 | Clark et al. |
| 5,713,946 A | 2/1998 | Ben-Haim |
| 5,715,822 A | 2/1998 | Watkins |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,728,047 A | 3/1998 | Edoga |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polyani |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,008 A | 9/1998 | Dekel et al. |

(56) References Cited

U.S. PATENT DOCUMENTS

| | | |
|---|---|---|
| 5,810,728 A | 9/1998 | Kuhn |
| 5,810,735 A | 9/1998 | Halperin et al. |
| 5,810,776 A * | 9/1998 | Bacich .............. A61B 17/3417 604/131 |
| 5,820,553 A | 10/1998 | Hughes |
| 5,820,591 A | 10/1998 | Thompson et al. |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,842,984 A | 12/1998 | Avitall |
| 5,843,051 A | 12/1998 | Adams et al. |
| 5,843,076 A | 12/1998 | Webster, Jr. et al. |
| 5,846,183 A | 12/1998 | Chilcoat |
| 5,848,967 A | 12/1998 | Cosman |
| 5,851,183 A | 12/1998 | Bucholz |
| 5,865,726 A | 2/1999 | Katsurada et al. |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,879,499 A | 3/1999 | Corvi |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,157 A | 4/1999 | Day et al. |
| 5,893,885 A | 4/1999 | Webster, Jr. |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,935,160 A | 8/1999 | Auricchio et al. |
| 5,938,603 A | 8/1999 | Ponzi |
| 5,938,609 A * | 8/1999 | Pomeranz .................... 600/439 |
| 5,938,694 A | 8/1999 | Jaraczewski et al. |
| 5,947,925 A | 9/1999 | Ashiya et al. |
| 5,947,980 A | 9/1999 | Jensen et al. |
| 5,947,981 A | 9/1999 | Cosman |
| 5,950,629 A | 9/1999 | Taylor et al. |
| 5,951,475 A | 9/1999 | Gueziec et al. |
| 5,951,571 A | 9/1999 | Audette |
| 5,954,647 A | 9/1999 | Bova et al. |
| 5,954,796 A | 9/1999 | McCarty et al. |
| 5,957,844 A | 9/1999 | Dekel et al. |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,004,269 A | 12/1999 | Crowley et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,024,695 A | 2/2000 | Taylor et al. |
| 6,035,229 A | 3/2000 | Silverstein et al. |
| 6,050,724 A | 4/2000 | Schmitz et al. |
| 6,059,718 A | 5/2000 | Taniguchi et al. |
| 6,061,588 A | 5/2000 | Thornton et al. |
| 6,063,022 A | 5/2000 | Ben-Haim |
| 6,071,288 A | 6/2000 | Carol et al. |
| 6,073,043 A | 6/2000 | Schneider |
| 6,076,008 A | 6/2000 | Bucholz |
| 6,086,529 A | 7/2000 | Arndt |
| 6,104,944 A | 8/2000 | Martinelli |
| 6,112,111 A | 8/2000 | Glantz |
| 6,117,070 A | 9/2000 | Akiba |
| 6,118,845 A | 9/2000 | Simon et al. |
| 6,122,538 A | 9/2000 | Sliwa, Jr. et al. |
| 6,122,541 A | 9/2000 | Cosman et al. |
| 6,131,396 A | 10/2000 | Duerr et al. |
| 6,134,003 A | 10/2000 | Tearney et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,171,303 B1 | 1/2001 | Ben-Haim et al. |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,183,444 B1 | 2/2001 | Glines et al. |
| 6,188,355 B1 | 2/2001 | Gilboa |
| 6,192,280 B1 | 2/2001 | Sommer et al. |
| 6,194,639 B1 | 2/2001 | Botella et al. |
| 6,200,262 B1 | 3/2001 | Ouchi |
| 6,201,387 B1 | 3/2001 | Govari |
| 6,203,493 B1 | 3/2001 | Ben-Haim |
| 6,203,497 B1 | 3/2001 | Dekel et al. |
| 6,210,362 B1 | 4/2001 | Ponzi |
| 6,210,378 B1 | 4/2001 | Ouchi |
| 6,211,666 B1 | 4/2001 | Acker |
| 6,213,995 B1 | 4/2001 | Steen et al. |
| 6,216,027 B1 | 4/2001 | Willis et al. |
| 6,223,067 B1 | 4/2001 | Vilsmeier |
| 6,226,543 B1 | 5/2001 | Gilboa et al. |
| 6,233,476 B1 | 5/2001 | Strommer et al. |
| 6,236,875 B1 | 5/2001 | Bucholz et al. |
| 6,246,231 B1 | 6/2001 | Ashe |
| 6,246,784 B1 | 6/2001 | Summers et al. |
| 6,253,770 B1 | 7/2001 | Acker et al. |
| 6,259,942 B1 | 7/2001 | Westermann et al. |
| 6,273,896 B1 | 8/2001 | Franck et al. |
| 6,285,902 B1 | 9/2001 | Kienzle, III et al. |
| 6,298,262 B1 | 10/2001 | Franck et al. |
| 6,306,097 B1 | 10/2001 | Park et al. |
| 6,314,310 B1 | 11/2001 | Ben-Haim et al. |
| 6,319,250 B1 | 11/2001 | Falwell et al. |
| 6,332,089 B1 | 12/2001 | Acker et al. |
| 6,335,617 B1 | 1/2002 | Osadchy et al. |
| 6,341,231 B1 | 1/2002 | Ferre et al. |
| 6,345,112 B1 | 2/2002 | Summers et al. |
| 6,351,659 B1 | 2/2002 | Vilsmeier |
| 6,355,027 B1 | 3/2002 | Le et al. |
| 6,366,799 B1 | 4/2002 | Acker et al. |
| 6,368,316 B1 | 4/2002 | Jansen et al. |
| 6,373,240 B1 | 4/2002 | Govari |
| 6,381,485 B1 | 4/2002 | Hunter et al. |
| 6,381,490 B1 | 4/2002 | Ostrovsky |
| 6,422,994 B1 | 7/2002 | Kaneko et al. |
| 6,423,009 B1 | 7/2002 | Downey et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,443,894 B1 | 9/2002 | Sumanaweera et al. |
| 6,445,943 B1 | 9/2002 | Ferre et al. |
| 6,447,504 B1 | 9/2002 | Ben-Haim et al. |

(56) References Cited

U.S. PATENT DOCUMENTS

| | | |
|---|---|---|
| 6,453,190 B1 | 9/2002 | Acker et al. |
| 6,468,265 B1 | 10/2002 | Evans et al. |
| 6,470,207 B1 | 10/2002 | Simon et al. |
| 6,474,341 B1 | 11/2002 | Hunter et al. |
| 6,478,802 B2 | 11/2002 | Kienzle, III et al. |
| 6,484,049 B1 | 11/2002 | Seeley et al. |
| 6,484,118 B1 | 11/2002 | Govari |
| 6,485,413 B1 | 11/2002 | Boppart et al. |
| 6,490,475 B1 | 12/2002 | Seeley et al. |
| 6,493,573 B1 | 12/2002 | Martinelli et al. |
| 6,498,944 B1 | 12/2002 | Ben-Haim et al. |
| 6,499,488 B1 | 12/2002 | Hunter et al. |
| 6,516,046 B1 | 2/2003 | Frohlich et al. |
| 6,527,443 B1 | 3/2003 | Vilsmeier et al. |
| 6,547,722 B1 | 4/2003 | Masakazu et al. |
| 6,551,325 B2 | 4/2003 | Neubauer et al. |
| 6,579,277 B1 | 6/2003 | Rabiner et al. |
| 6,580,938 B1 | 6/2003 | Acker |
| 6,584,174 B2 | 6/2003 | Schubert et al. |
| 6,585,639 B1 | 7/2003 | Kotmel et al. |
| 6,591,129 B1 | 7/2003 | Ben-Haim et al. |
| 6,593,884 B1 | 7/2003 | Gilboa et al. |
| 6,609,022 B2 | 8/2003 | Vilsmeier et al. |
| 6,611,700 B1 | 8/2003 | Vilsmeier et al. |
| 6,618,612 B1 | 9/2003 | Acker et al. |
| 6,628,980 B2 | 9/2003 | Atalar et al. |
| 6,640,128 B2 | 10/2003 | Vilsmeier et al. |
| 6,650,927 B1 | 11/2003 | Keidar |
| 6,666,864 B2 | 12/2003 | Bencini et al. |
| 6,676,659 B2 | 1/2004 | Hutchins et al. |
| 6,690,963 B2 | 2/2004 | Ben-Haim et al. |
| 6,694,162 B2 | 2/2004 | Hartlep |
| 6,701,179 B1 | 3/2004 | Martinelli et al. |
| 6,706,041 B1 | 3/2004 | Costantino |
| 6,711,429 B1 | 3/2004 | Gilboa et al. |
| 6,712,842 B1 | 3/2004 | Gifford, III et al. |
| 6,751,492 B2 | 6/2004 | Ben-Haim |
| 6,770,027 B2 | 8/2004 | Banik et al. |
| 6,788,967 B2 | 9/2004 | Ben-Haim et al. |
| 6,796,963 B2 | 9/2004 | Carpenter et al. |
| 6,887,236 B2 | 3/2005 | Gilboa |
| 6,947,788 B2 | 9/2005 | Gilboa et al. |
| 6,960,161 B2 | 11/2005 | Amling et al. |
| 6,995,729 B2 | 2/2006 | Govari et al. |
| 7,022,066 B2 | 4/2006 | Yokoi et al. |
| 7,101,380 B2 | 9/2006 | Khachin et al. |
| 7,182,756 B2 | 2/2007 | Saeed et al. |
| 7,197,354 B2 | 3/2007 | Sobe |
| 7,231,820 B2 | 6/2007 | Gilboa |
| 7,236,567 B2 | 6/2007 | Sandkamp et al. |
| 7,286,868 B2 | 10/2007 | Govari |
| 7,301,332 B2 | 11/2007 | Govari et al. |
| 7,321,228 B2 | 1/2008 | Govari |
| 7,324,915 B2 | 1/2008 | Altmann et al. |
| 7,343,195 B2 | 3/2008 | Strommer et al. |
| 7,353,125 B2 | 4/2008 | Nieminen et al. |
| 7,357,795 B2 | 4/2008 | Kaji et al. |
| 7,366,562 B2 | 4/2008 | Dukesherer et al. |
| 7,370,656 B2 | 5/2008 | Gleich et al. |
| 7,373,271 B1 | 5/2008 | Schneider |
| 7,386,339 B2 | 6/2008 | Strommer et al. |
| 7,397,364 B2 | 7/2008 | Govari |
| 7,399,296 B2 | 7/2008 | Poole et al. |
| 7,497,029 B2 | 3/2009 | Plassky et al. |
| 7,505,809 B2 | 3/2009 | Strommer et al. |
| 7,536,218 B2 | 5/2009 | Govari et al. |
| RE40,852 E | 7/2009 | Martinelli et al. |
| 7,570,987 B2 | 8/2009 | Raabe et al. |
| 7,577,474 B2 | 8/2009 | Vilsmeier |
| 7,579,837 B2 | 8/2009 | Fath et al. |
| 7,587,235 B2 | 9/2009 | Wist et al. |
| 7,599,535 B2 | 10/2009 | Kiraly et al. |
| 7,599,810 B2 | 10/2009 | Yamazaki |
| 7,630,753 B2 | 12/2009 | Simon et al. |
| 7,634,122 B2 | 12/2009 | Bertram et al. |
| 7,636,595 B2 | 12/2009 | Marquart et al. |
| 7,641,609 B2 | 1/2010 | Ohnishi et al. |
| 7,648,458 B2 | 1/2010 | Niwa et al. |
| 7,652,468 B2 | 1/2010 | Kruger et al. |
| 7,657,300 B2 | 2/2010 | Hunter et al. |
| 7,659,912 B2 | 2/2010 | Akimoto et al. |
| 7,660,623 B2 | 2/2010 | Hunter et al. |
| 7,680,528 B2 | 3/2010 | Pfister et al. |
| 7,684,849 B2 | 3/2010 | Wright et al. |
| 7,686,767 B2 | 3/2010 | Maschke |
| 7,688,064 B2 | 3/2010 | Shalgi et al. |
| 7,696,899 B2 | 4/2010 | Immerz et al. |
| 7,697,972 B2 | 4/2010 | Verard et al. |
| 7,697,973 B2 | 4/2010 | Strommer et al. |
| 7,697,974 B2 | 4/2010 | Jenkins et al. |
| 7,720,517 B2 | 5/2010 | Drysen |
| 7,722,565 B2 | 5/2010 | Wood et al. |
| 7,725,154 B2 | 5/2010 | Beck et al. |
| 7,725,164 B2 | 5/2010 | Suurmond et al. |
| 7,727,269 B2 | 6/2010 | Abraham-Fuchs et al. |
| 7,729,742 B2 | 6/2010 | Govari |
| 7,744,605 B2 | 6/2010 | Vilsmeier et al. |
| 7,747,307 B2 | 6/2010 | Wright et al. |
| 7,751,865 B2 | 7/2010 | Jascob et al. |
| 7,998,062 B2 * | 8/2011 | Gilboa ............................ 600/117 |
| 8,016,749 B2 * | 9/2011 | Clerc et al. .................... 600/117 |
| 2001/0004676 A1 | 6/2001 | Ouchi |
| 2001/0007918 A1 | 7/2001 | Vilsmeier et al. |
| 2001/0007925 A1 | 7/2001 | Ritchart et al. |
| 2001/0031919 A1 | 10/2001 | Strommer et al. |
| 2001/0034530 A1 | 10/2001 | Malackowski et al. |
| 2001/0036245 A1 | 11/2001 | Kienzle, III et al. |
| 2002/0026097 A1 | 2/2002 | Akiba |
| 2002/0067408 A1 | 6/2002 | Adair et al. |
| 2002/0087100 A1 | 7/2002 | Onuki et al. |
| 2002/0095081 A1 | 7/2002 | Vilsmeier |
| 2002/0128565 A1 | 9/2002 | Rudy |
| 2002/0137014 A1 | 9/2002 | Anderson et al. |
| 2002/0162555 A1 | 11/2002 | West et al. |
| 2002/0165503 A1 | 11/2002 | Morris et al. |
| 2002/0173689 A1 | 11/2002 | Kaplan |
| 2002/0193686 A1 | 12/2002 | Gilboa |
| 2003/0018251 A1 | 1/2003 | Solomon |
| 2003/0028096 A1 | 2/2003 | Niwa et al. |
| 2003/0040657 A1 | 2/2003 | Yamaya |
| 2003/0074011 A1 | 4/2003 | Gilboa et al. |
| 2003/0086599 A1 | 5/2003 | Armato et al. |
| 2003/0114742 A1 | 6/2003 | Lewkowicz et al. |
| 2003/0142753 A1 | 7/2003 | Gunday |
| 2003/0160721 A1 | 8/2003 | Gilboa et al. |
| 2003/0171653 A1 | 9/2003 | Yokoi et al. |
| 2003/0227547 A1 | 12/2003 | Iddan |
| 2004/0015049 A1 | 1/2004 | Zaar |
| 2004/0024309 A1 | 2/2004 | Ferre et al. |
| 2004/0086161 A1 | 5/2004 | Sivaramakrishna et al. |
| 2004/0097804 A1 | 5/2004 | Sobe |
| 2004/0138548 A1 | 7/2004 | Strommer et al. |
| 2004/0169509 A1 | 9/2004 | Czipott et al. |
| 2004/0249267 A1 | 12/2004 | Gilboa |
| 2004/0260201 A1 | 12/2004 | Mueller, Jr. |
| 2005/0033149 A1 | 2/2005 | Strommer et al. |
| 2005/0059890 A1 | 3/2005 | Deal et al. |
| 2005/0080342 A1 | 4/2005 | Gilreath et al. |
| 2005/0085715 A1 | 4/2005 | Dukesher et al. |
| 2005/0090818 A1 | 4/2005 | Pike, Jr. et al. |
| 2005/0107688 A1 | 5/2005 | Strommer |
| 2005/0119527 A1 | 6/2005 | Banik et al. |
| 2005/0182292 A1 | 8/2005 | Suzuki |
| 2005/0182295 A1 | 8/2005 | Soper et al. |
| 2005/0197566 A1 | 9/2005 | Strommer et al. |
| 2005/0229934 A1 | 10/2005 | Willeford |
| 2006/0015126 A1 | 1/2006 | Sher |
| 2006/0058647 A1 | 3/2006 | Strommer et al. |
| 2006/0064006 A1 | 3/2006 | Strommer et al. |
| 2006/0069313 A1 | 3/2006 | Couvillon, Jr. et al. |
| 2006/0149134 A1 | 7/2006 | Soper et al. |
| 2006/0184016 A1 | 8/2006 | Glossop |
| 2006/0235458 A1 * | 10/2006 | Belson ............ A61M 25/0032 606/191 |

(56) References Cited

U.S. PATENT DOCUMENTS

| | | |
|---|---|---|
| 2007/0163597 A1 | 7/2007 | Mikkaichi et al. |
| 2007/0167714 A1 | 7/2007 | Kiraly et al. |
| 2007/0167738 A1 | 7/2007 | Timinger et al. |
| 2007/0167743 A1 | 7/2007 | Honda et al. |
| 2007/0167806 A1 | 7/2007 | Wood et al. |
| 2007/0225559 A1 | 9/2007 | Clerc et al. |
| 2007/0265639 A1 | 11/2007 | Danek et al. |
| 2007/0287901 A1 | 12/2007 | Strommer et al. |
| 2007/0293721 A1 | 12/2007 | Gilboa |
| 2008/0086051 A1 | 4/2008 | Voegele |
| 2008/0097187 A1 | 4/2008 | Gielen et al. |
| 2008/0118135 A1 | 5/2008 | Averbuch et al. |
| 2008/0125760 A1 | 5/2008 | Gilboa |
| 2008/0132757 A1 | 6/2008 | Tgavalekos |
| 2008/0132909 A1 | 6/2008 | Jascob et al. |
| 2008/0132911 A1 | 6/2008 | Sobe |
| 2008/0139886 A1 | 6/2008 | Tatsuyama |
| 2008/0139915 A1 | 6/2008 | Dolan et al. |
| 2008/0144909 A1 | 6/2008 | Wiemker et al. |
| 2008/0147000 A1 | 6/2008 | Seibel et al. |
| 2008/0154172 A1 | 6/2008 | Mauch |
| 2008/0157755 A1 | 7/2008 | Kruger et al. |
| 2008/0161682 A1 | 7/2008 | Kendrick et al. |
| 2008/0162074 A1 | 7/2008 | Schneider |
| 2008/0183071 A1 | 7/2008 | Strommer et al. |
| 2008/0185672 A1* | 8/2008 | Jacobsen .............. A61B 1/05 257/432 |
| 2008/0188749 A1 | 8/2008 | Rasche et al. |
| 2009/0182224 A1 | 7/2009 | Shmarak et al. |
| 2009/0234223 A1 | 9/2009 | Onoda et al. |
| 2009/0318797 A1 | 12/2009 | Hadani |
| 2010/0016757 A1 | 1/2010 | Greenburg et al. |

FOREIGN PATENT DOCUMENTS

| | | |
|---|---|---|
| DE | 3508730 A1 | 9/1986 |
| DE | 3520782 A1 | 12/1986 |
| DE | 3717871 A1 | 12/1988 |
| DE | 3831278 A1 | 3/1989 |
| DE | 3838011 A1 | 7/1989 |
| DE | 4213426 A1 | 10/1992 |
| DE | 4225112 C1 | 12/1993 |
| DE | 4233978 C1 | 4/1994 |
| DE | 09-253038 A | 9/1997 |
| DE | 19610984 A1 | 9/1997 |
| DE | 19715202 A1 | 10/1998 |
| DE | 19751761 A1 | 10/1998 |
| DE | 19832296 A1 | 2/1999 |
| DE | 19747427 A1 | 5/1999 |
| DE | 10085137 T1 | 11/2002 |
| EP | 0062941 A1 | 10/1982 |
| EP | 0119660 A1 | 9/1984 |
| EP | 0155857 A2 | 9/1985 |
| EP | 0319844 A1 | 6/1989 |
| EP | 0326768 A2 | 8/1989 |
| EP | 0350996 A1 | 1/1990 |
| EP | 0419729 A1 | 4/1991 |
| EP | WO91/03982 A1 | 4/1991 |
| EP | 0427358 A1 | 5/1991 |
| EP | 0456103 A2 | 11/1991 |
| EP | 0581704 A1 | 2/1994 |
| EP | 0600610 A2 | 6/1994 |
| EP | 0894473 A2 | 8/1994 |
| EP | 0651968 A1 | 5/1995 |
| EP | 0796633 A1 | 9/1997 |
| EP | 0908146 A2 | 10/1997 |
| EP | 0930046 A2 | 11/1997 |
| EP | 0655138 B1 | 4/1998 |
| EP | 10-197807 A | 7/1998 |
| EP | 0857461 A2 | 8/1998 |
| EP | 0894473 A2 | 2/1999 |
| EP | 1078644 A1 | 8/1999 |
| EP | 1255113 A1 | 6/2002 |
| EP | 1543765 A1 | 6/2005 |
| EP | 1667749 B1 | 8/2009 |
| EP | 2096523 A1 | 9/2009 |
| FR | 2417970 A1 | 9/1979 |
| FR | 2618211 A1 | 1/1989 |
| GB | 2094590 A | 9/1982 |
| GB | 2164856 A | 4/1986 |
| JP | 63-240851 A1 | 10/1988 |
| JP | 03-267054 A | 11/1991 |
| JP | 06-125869 A | 5/1994 |
| JP | 06194639 A | 7/1994 |
| JP | 07-043619 A | 2/1995 |
| JP | 2000-075218 A | 3/2000 |
| JP | 2001-231743 A | 8/2001 |
| JP | 2001-275942 A | 10/2001 |
| WO | WO88/09151 A1 | 12/1988 |
| WO | WO89/05123 A1 | 6/1989 |
| WO | WO90/05494 A1 | 5/1990 |
| WO | WO91/04711 A1 | 4/1991 |
| WO | WO91/07726 A1 | 5/1991 |
| WO | WO92/03090 A1 | 3/1992 |
| WO | WO92/06645 A1 | 4/1992 |
| WO | WO94/04938 A1 | 3/1994 |
| WO | WO94/23647 A1 | 10/1994 |
| WO | WO94/24933 A1 | 11/1994 |
| WO | WO95/07055 A1 | 3/1995 |
| WO | WO96/11624 A1 | 4/1996 |
| WO | WO96/32059 A1 | 10/1996 |
| WO | WO97/29682 A1 | 8/1997 |
| WO | WO97/29684 A1 | 8/1997 |
| WO | WO97/36192 A1 | 10/1997 |
| WO | WO97/49453 A1 | 12/1997 |
| WO | WO98/08554 A1 | 3/1998 |
| WO | WO98/38908 A1 | 9/1998 |
| WO | WO99/15097 A1 | 4/1999 |
| WO | WO99/21498 A1 | 5/1999 |
| WO | WO99/23956 A1 | 5/1999 |
| WO | WO99/26549 A1 | 6/1999 |
| WO | WO99/27839 A1 | 6/1999 |
| WO | WO99/29253 A1 | 6/1999 |
| WO | WO99/33406 A1 | 7/1999 |
| WO | WO99/37208 A1 | 7/1999 |
| WO | WO99/38449 A1 | 8/1999 |
| WO | WO99/52094 A1 | 10/1999 |
| WO | WO99/60939 A1 | 12/1999 |
| WO | WO00/06701 A1 | 2/2000 |
| WO | WO00/14056 A1 | 3/2000 |
| WO | WO00/16684 A1 | 3/2000 |
| WO | WO00/35531 A1 | 6/2000 |
| WO | 2000-279379 A | 10/2000 |
| WO | WO01/19235 A1 | 3/2001 |
| WO | WO01/30437 A1 | 5/2001 |
| WO | WO01/91842 A1 | 6/2001 |
| WO | WO01/67035 A1 | 9/2001 |
| WO | WO01/87136 A2 | 11/2001 |
| WO | WO01/87398 A2 | 11/2001 |
| WO | WO02/24054 A2 | 3/2002 |
| WO | WO02/64011 A2 | 8/2002 |
| WO | WO02/70047 A1 | 9/2002 |
| WO | WO03/86498 A2 | 10/2003 |
| WO | WO04/23986 A1 | 3/2004 |
| WO | WO05/25635 A2 | 3/2005 |
| WO | WO05/074380 A2 | 8/2005 |
| WO | WO06/116597 A2 | 11/2006 |
| WO | WO07/109418 A2 | 9/2007 |

OTHER PUBLICATIONS

European Patent Office, Decision to Grant dated Apr. 13, 2012 in European Patent Application No. 10191689, 1 page.

United States Patent and Trademark Office, Office Action dated Feb. 22, 2012 in U.S. Appl. No. 12/233,933, 10 pages.

European Patent Office, Extended European Search Report dated Feb. 20, 2012 in European Patent Application No. 06701745, 9 pages.

United States Patent and Trademark Office, Final Office Action dated Dec. 19, 2011 in U.S. Appl. No. 10/571,793, 8 pages.

(56) References Cited

OTHER PUBLICATIONS

European Patent Office, Extended European Search Report dated Nov. 22, 2011 in European Patent Application No. 11182823, 5 pages.
European Patent Office, Extended European Search Report dated Nov. 21, 2011 in European Patent Application No. 11182823, 5 pages.
United States Patent and Trademark Office, Office Action dated Nov. 18, 2011 in U.S. Appl. No. 12/476,976, 8 pages.
WIPO, U.S. International Search Authority, International Search Report and Written Opinion dated Oct. 7, 2011 in International Patent Application No. PCT/US2011/040579, 8 pages.
European Patent Office, Extended European Search Report dated Sep. 6, 2011 in European Patent Application No. 03719056, 6 pages.
European Patent Office, Extended European Search Report dated Sep. 6, 2011 in European Patent Application No. 11174666, 6 pages
Japanese Patent Office, Official Action dated Aug. 23, 2011 in Japanese Patent Application No. 2007-552806, 7 pages.
Japanese Patent Office, Examiner's Report dated Aug. 19, 2011 in Japanese Patent Application No. JP2007-552806, 7 pages.
WIPO, U.S. International Preliminary Examining Authority, International Preliminary Report on Patentability dated Jun. 30, 2011 in International Patent Application No. PCT/US2009/069073, 6 pages.
United States Patent and Trademark Office, Office Action dated May 24, 2011 in U.S. Appl. No. 10/571,793, 8 pages.
United States Patent and Trademark Office, Office Action dated Mar. 31, 2011 in U.S. Appl. No. 12/643,917, 10 pages.
European Patent Office, Extended European Search Report dated Mar. 8, 2011 in European Patent Application No. 10191689, 4 pages.
United States Patent and Trademark Office, Office Action dated Dec. 23, 2010 in U.S. Appl. No. 10/571,793, 11 pages.
European Patent Office, Supplementary European Search Report dated Nov. 15, 2010 in European Patent Application No. EP10159373.9, 12 pages.
United States Patent and Trademark Office, Office Action dated Oct. 4, 2010 in U.S. Appl. No. 12/271,175, 11 pages.
European Patent Office, Examination Report dated Sep. 11, 2010 in European Patent Application No. 3719056, 4 pages.
United States Patent and Trademark Office, Final Office Action dated Jun. 23, 2010 in U.S. Appl. No. 10/571,793, 10 pages.
WIPO, U.S. International Search Authority, International Search Report and Written Opinion dated Apr. 23, 2010 in International Patent Application No. PCT/US2009/069073, 8 pages.
WIPO, U.S. International Preliminary Examining Authority, International Preliminary Report on Patentability dated Apr. 8, 2010 in International Patent Application No. PCT/IB2008/002543, 7 pages.
European Patent Office, Examination Report dated Mar. 30, 2010 in European Patent Application No. EP05737664.2, 5 pages.
Japanese Patent Office, Official Action dated Mar. 12, 2010 in Japanese Patent Application No. 2006-526007, 5 pages.
European Patent Office, Extended European Search Report dated Dec. 1, 2009 in European Patent Application No. 09157586, 7 pages.
United States Patent and Trademark Office, Office Action dated Nov. 27, 2009 in U.S. Appl. No. 10/571,793, 11 pages.
WIPO, U.S. International Search Authority, International Search Report and Written Opinion dated Nov. 12, 2009 in International Patent Application No. PCT/IL2009/000697, 9 pages.
WIPO, U.S. International Search Authority, International Search Report and Written Opinion dated Nov. 22, 2009 in International Patent Application No. PCT/IL2009/000553, 7 pages.
WIPO, U.S. International Preliminary Examining Authority, International Preliminary Report on Patentability dated Jul. 28, 2009 in International Patent Application No. PCT/IL2005/000159, 6 pages.
European Patent Office, Examination Report dated Jul. 14, 2009 in European Patent Application No. 03719056, 6 pages.
United States Patent and Trademark Office, Office Action dated Jun. 24, 2009 in U.S. Appl. No. 10/571,695, 11 pages.

WIPO, U.S. International Preliminary Examining Authority, International Preliminary Report on Patentability dated Mar. 30, 2009 in International Patent Application No. PCT/IL2006/000113, 6 pages.
WIPO, U.S. International Search Authority, International Search Report and Written Opinion dated Mar. 16, 2009 in International Patent Application No. PCT/IB2008/002543, 9 pages.
United States Patent and Trademark Office, Final Office Action dated Mar. 12, 2009 in U.S. Appl. No. 10/597,747, 7 pages.
European Patent Office, Supplementary European Search Report dated Feb. 27, 2009 in European Patent Application No. 03719056, 6 pages.
European Patent Office, Decision to Grant dated Feb. 20, 2009 in European Patent Application No. 04770514, 24 pages.
WIPO, U.S. International Search Authority, International Search Report and Written Opinion dated Dec. 15, 2008 in International Patent Application No. PCT/IL2006/000113, 6 pages.
Japanese Patent Office, Official Action dated Dec. 12, 2008 in Japanese Patent Application No. 2008-583508, 9 pages.
European Patent Office, Supplementary European Search Report dated Oct. 7, 2008 in European Patent Application No. 04770514, 4 pages.
European Patent Office, Supplementary European Search Report dated Sep. 18, 2008 in European Patent Application No. EP0477514.1, 4 pages.
United States Patent and Trademark Office, Office Action dated Sep. 11, 2008 in U.S. Appl. No. 10/597,747, 9 pages.
WIPO, U.S. International Search Authority, International Search Report and Written Opinion dated Jul. 11, 2008 in International Patent Application No. PCT-IL2005/000159, 12 pages.
WIPO, U.S. International Preliminary Examining Authority, International Preliminary Report on Patentability dated Oct. 9, 2007 in International Patent Application No. PCT/IL2004/000843, 4 pages.
WIPO, U.S. International Search Authority, International Search Report and Written Opinion dated Sep. 24, 2007 in International Patent Application No. PCT/IL2004/000843, 4 pages.
WIPO, U.S. International Search Authority, International Search Report and Written Opinion dated Jul. 11, 2007 in International Patent Application. No. PCT/IL2005/000159, 6 pages.
United States Patent and Trademark Office, Notice of Allowance dated Oct. 6, 2006 in U.S. Appl. No. 10/491,099, 7 pages.
China Patent and Trademark Office, Office Action dated Jun. 19, 2006 in Chinese Patent Application No. 038135485, 5 pages.
United States Patent and Trademark Office, Office Action dated Dec. 30, 2005 in U.S. Appl. No. 10/491,099, 15 pages.
United States Patent and Trademark Office, Office Action dated Apr. 22, 2005 in U.S. Appl. No. 10/491,099, 5 pages.
United States Patent and Trademark Office, Notice of Allowance dated Jan. 3, 2005 in U.S. Appl. No. 10/137,415, 9 pages.
Shmarak, I. et al., U.S. Appl. No. 10/986,567, filed Nov. 2004 (abandoned, unpublished), 84 pages.
United States Patent and Trademark Office, Office Action dated Jul. 1, 2004 in U.S. Appl. No. 10/10,137,415, 14 pages.
WIPO, U.S. International Preliminary Examining Authority, International Preliminary Report on Patentability dated Jan. 24, 2004 in International Patent Application No. PCT/IL2003/000323, 3 pages.
WIPO, U.S. International Search Authority, International Search Report dated Dec. 8, 2003 in International Patent Application No. PCT/IL2003/000323, 1 page.
Stenoien, D.L. et al., "Ligang-Mediated Assembly and Real-Time Cellular Dynamics of Estrogen Receptor α-Coactivator Complexes in Living Cells," *Molecular and Cellular Biology*, Jul. 2001, pp, 4404-4412, 9 pages.
McKenna, N.J. et al., "Nuclear Receptor Coreglators: Cellular and Molecular Biology," *Endocrine Reviews*. 20(3): 321-344, Jun. 1, 1999, 24 pages.
Ding, X.F. et al., "Nuclear Receptor-Binding Sites of Coactivators Glucocorticoid Receptor Interacting Protein I (GRIP1) and Steroid Receptor Coactivator 1. (SRC--1): Multiple Motifs with Different Binding Specificities," *Molecular Endocrinlogy* 12:302-313, Feb. 1, 1998 (9 pages).

* cited by examiner

LOCATABLE EXPANDABLE WORKING CHANNEL AND METHOD

RELATED APPLICATIONS

This application claims priority to U.S. Provisional Application Ser. No. 61/355,115 filed Jun. 15, 2010 entitled Locatable Expandable Working Channel, which is hereby incorporated herein by reference in its entirety.

FIELD OF THE INVENTION

The present invention relates to catheters or elongated working channels for use in medical procedures. More particularly, the present invention relates to a locatable probe designed to be deployed through the working channel of a bronchoscope and providing an expandable pathway to a distal target.

BACKGROUND OF THE INVENTION

Catheters or elongated working channels are a staple device in performing noninvasive medical procedure. The advantages of noninvasive procedures are numerous and include decreased risk of infection, decreased tissue damage, and shorter recovery periods. Unfortunately, the types of procedures that can be preformed utilizing noninvasive techniques is often limited by the size of the body lumen through which the procedure will be conducted and, to an equal extent, the size of the catheter or working channel inserted into the body lumen through which the tools for conducting the procedures will be passed through.

Catheters or elongated working channels are often supplied in standard sizes specific to a particular medical field or application. For example, in procedures involving the lung or bronchial tree, a bronchoscope is typically employed to span from the mouth, through the trachea, to proximal locations in the primary branches of the bronchial tree. Bronchoscopes generally have within their structure a working channel through which devices may be passed to access and perform procedures within the lungs. This working channel typically has an inner diameter of 2.8 mm. Therefore, all noninvasive pulmonary procedures utilizing a bronchoscope are limited to employing only those tools and devices that can fit within a 2.8 mm working channel.

Due to the size limitation of the bronchoscope's working channel, it is often necessary for a physician to pass a first tool or device through the working channel, retract the first device, pass a second device through the channel, and repeat this process several times with either the same or different devices. This method not only lengthens the procedure time but also introduces the possibility that the bronchoscope or elongated working channel through which devices are passed may migrate from their desired locations.

This limited working channel diameter not only dictates the size of the tools and devices a physician can use but also the size of tissue samples that may be obtained from a patient. Again, in the case of bronchoscopes, in order to obtain a sample of tissue at a point of interest, an extended working channel is typically passed through the working channel of the bronchoscope and positioned proximate to the point of interest. The extended working channel (or "EWC") is a catheter having an outside diameter of less than 2.8 mm. A biopsy needle is then passed through the EWC, used to extract the sample, and retracted from the channel. Because the EWC has an outside diameter of less than 2.8 mm, it follows that the inside diameter of the EWC is significantly smaller. Due to the limited diameter of the EWC, the biopsy device will necessarily be quite small. As a result the tissue sample obtained will also be very small. The limited size of the tissue samples that can be obtained in this manner, in turn, often necessitate repeating the tissue extraction and sampling process several times in order to obtain a reasonable representation of the tissue characteristics within the area of interest.

In the case of bronchoscopes, the 2.8 mm diameter limitation is not dictated by the constraints and characteristics of the bronchial tree. To the contrary, the tissue forming the airways of the bronchial tree are quite elastic, distal of the cartilagenous zone. These lumens are safely, and easily expanded and capable of receiving catheters and elongated working channels of significantly greater diameters than currently used. The risk of trauma does not arise from radially stretching the airways. Rather, injury is more likely to be caused by longitudinally advancing a relatively large, less flexible device through the airways, thereby placing undue axial, rather than radial, pressure on the airways and branches.

There is a need in the field for a catheter or EWC that can be initially passed through the working channel of a conventional endoscope, bronchoscope or similar device but that upon placement, may radially expand once deployed within the body lumen. Thereby providing a elongated working channel through which a physician may simultaneously pass multiple tools or devices, larger tools or devices, and extract larger tissue samples.

Ideally, this EWC would also be locatable by a three-dimensional navigation system. The working channel of a bronchoscope ends at the distal end of the bronchoscope, which is also where the lens of the scope is located. The working channel allows a physician to access tissue with a tool while watching the tool through the scope. Using an EWC however, often extends the tool past the viewing range of the scope. This is especially true in the lungs where the airways narrow quickly, preventing the use of the scope in the distal airways.

Three dimensional tracking technology has allowed an EWC to be safely and accurately navigated into the distal airways, well past the reach of the bronchoscope. This tracking technology typically utilizes a small location sensor, preferably providing tracking data in six degrees of freedom, at a distal tip of a probe. Suitable sensors, sensing techniques and related methods and devices are disclosed in U.S. Pat. Nos. 6,188,355; 6,226,543; 6,558,333; 6,574,498; 6,593,884; 6,615,155; 6,702,780; 6,711,429; 6,833,814; 6,974,788; and 6,996,430, all to Gilboa or Gilboa et al.; and U.S. Published Applications Pub. Nos. 2002/0193686; 2003/0074011; 2003/0216639; 2004/0249267 to either Gilboa or Gilboa et al. All of these references are incorporated herein in their entireties.

OBJECTS AND SUMMARY OF THE INVENTION

A device and method for allowing the placement of a larger biopsy tool at distal locations in a branched structure while still utilizing the working channel of a standard bronchoscope. The device includes a locatable probe that can be extended out of the working channel and navigated distally therefrom. The probe includes a lumen formed of an expandable material that essentially provides a radially expanding EWC.

In certain embodiments, the radially expandable working channel or catheter may further employ an anchoring mechanism for securing a distal end of the device within a patient lumen.

BRIEF DESCRIPTION OF THE DRAWINGS

These and other aspects, features and advantages of which embodiments of the invention are capable of will be apparent and elucidated from the following description of embodiments of the present invention, reference being made to the following drawings.

DESCRIPTION OF EMBODIMENTS

Figure 1:
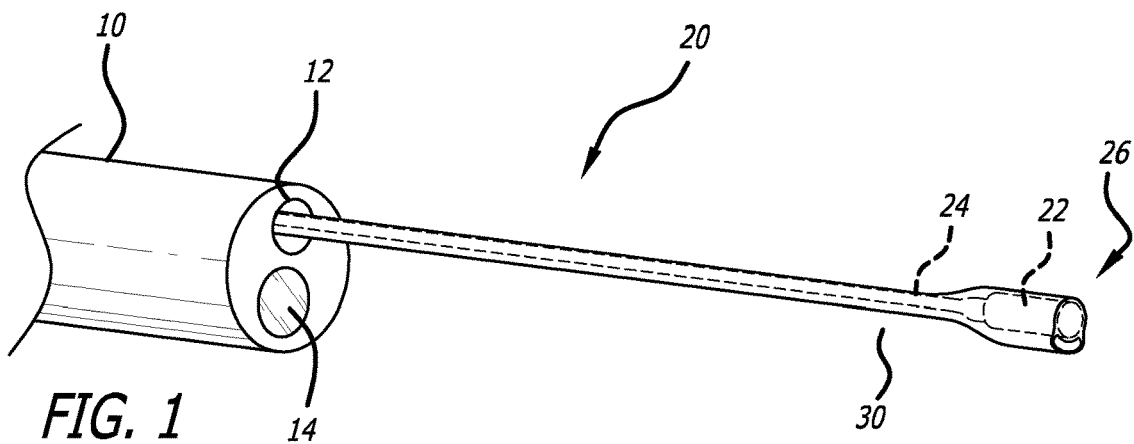
FIG. 1 is perspective view of a preferred embodiment of a device according to the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Referring now to FIG. 1, there is shown an embodiment of a device 20 of the present invention, extending through a standard bronchoscope 10. The bronchoscope 10 is shown as having a working channel 12 and an optical lens 14. It is understood, however, that the bronchoscope 10 shown is just an illustrative representation of a standard bronchoscope having a working channel 12 and that the present invention 20 is designed for use with any bronchoscope or endoscope.

Figure 2:
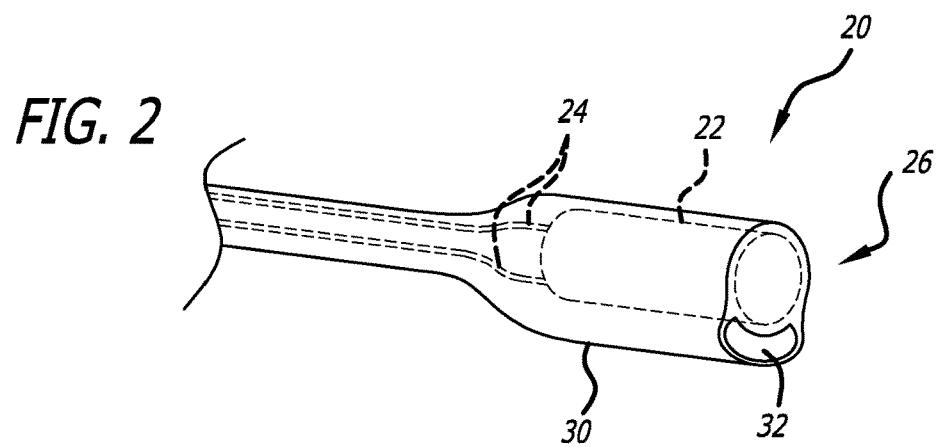
FIG. 2 is a perspective view of a distal end of a preferred embodiment of a device according to the present invention.

The device 20 generally includes a sensor 20, sensor wires 24, and a flexible sheath 30. The sheath 30 encompasses the sensor 22 and the wires 24. Preferably, the sheath 30 encases the sensor 22 and the wires 24 within a wall of the sheath 30. The remaining material of the sheath forms a thin, flexible wall around an expandable lumen 32, shown best in FIG. 2, which is an enlarged view of a distal end 26 of the device 20.

Figure 3:
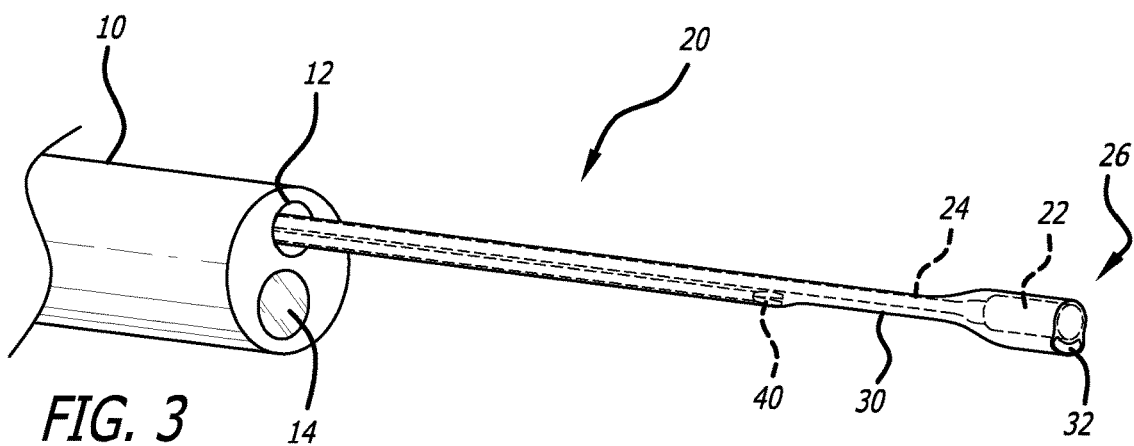
FIG. 3 is a perspective view of a preferred embodiment of A device according to the present invention with a biopsy tool being passed therethrough.

FIG. 3 shows the device 20 being extended from the working channel 12 of a bronchoscope 10. As shown, once the sensor 22 exits the working channel 12, the wires 24 and the sheath 30 are all that remain in the working channel 12. Due to the small profile of the wires 24, and the thin, flexible nature of the sheath 30, nearly all of the 2.8 mm working channel lumen remains available for passing a tool, such as a biopsy tool, therethrough.

In FIG. 3 a tool 40 is shown in phantom lines passing through the lumen 32 of the device 20 of the present invention. The sheath 30 stretches to accommodate the tool 40 as the tool passes through the lumen 32. Preferably, in order to facilitate smooth passage of the tool 40, the sheath 30 is constructed of a biologically friendly, expandable material that is also strong as well as slippery. Non-limiting examples of acceptable materials include: polyamide, polyethylene, polyurethane, polyester, pylon, and silicone.

The body of the device 20, proximal of the sensor 22, is contemplated as being limited to merely the wires 24, leading to and from the sensor 22, and the sheath 30 material. Keeping the body limited to these components reduces the profile. Additionally, however, it may be desirable to provide the device with at least some steerability. As such, the wires 24, sheath 30, or both may be either formed with a gentle curve, provided with a steering wire.

In one embodiment, steerability is provided by using the wires 24 as steering wires. By gently pulling one wire relative to the other, the sensor 22 turns slightly in the direction of the pulled wire. The proximal ends of the wire may be fed through a prior art steering device to effect this, as long as connection is made to a navigation system.

In operation, certain embodiments of the present invention may be utilized in conjunction with conventional medical endoscopes. For example, the above described embodiments may conform to an initial non-expanded outer diameter less than that of the interior diameter of the working channel of a endoscope such as, for example, a bronchoscope. The radially expandable EWC may first be passed through the working channel of the bronchoscope, optionally using said sensor to assist in navigation of said expandable EWC. The distal end of the EWC may then be anchored proximate to a point of interest within the patient. Once the EWC is secured at the point of interest, the bronchoscope may be withdrawn over the anchored EWC from the patient's airway. With the constraint of the bronchoscope's limited diameter working channel removed, the physician may proceed with expanding and/or passing the desire devices and tools through the radially expandable EWC.

Alternatively, radially expandable EWCs according to the present invention may also be employed without the aid or otherwise absent a conventional endoscope. For example, a guidewire or steerable catheter may simply be navigated to the point of interest within the patient. The radially expandable EWC may then be passed over the guidewire or steerable catheter. The physician may then anchor the EWC proximate to the region of interest and proceed with expanding and/or passing the desire devices and tools through the radially expandable EWC.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

I claim:

1. A radially expandable device configured for insertion through a working channel of an endoscope, the radially expandable device comprising:

a location mechanism generating location information pertaining to a location of the radially expandable device, the location mechanism including a three dimensional (3D) tracking sensor that provides tracking data in six degrees of freedom disposed at a distal portion of the radially expandable device, the 3D tracking sensor connected to wires leading from the 3D tracking sensor to a proximal end of the radially expandable device, the wires utilized to carry a signal from the 3D tracking sensor and to deflect a distal end of the radially expandable device when at least one of the wires is actuated; and a flexible sheath defining a channel therein,
wherein the channel is deformable along its entire length, from an unexpanded configuration to a radially expanded configuration, such that when a tool is inserted through the channel, the channel transitions from the unexpanded configuration to the radially expanded configuration along its entire length as the tool traverses the channel, and wherein the sensor and the wires are within a wall of the flexible sheath.

2. The radially expandable device of claim 1, wherein the flexible sheath comprises a material selected from the group consisting of: polyamide, polyethylene, polyurethane, polyester, pylon and silicone.

3. The radially expandable device of claim 1, wherein the wires have a curved configuration.

4. The radially expandable device of claim 1, wherein the flexible sheath has a curved configuration.

5. The radially expandable device of claim 1, wherein the radially expandable device has a curved configuration.

6. The radially expandable device of claim 1, wherein the wires are configured to move relative to each other to deflect the distal portion of the radially expandable device.

7. The radially expandable device of claim 1, wherein the flexible sheath encases the sensor and the wires within a wall of the flexible sheath.

8. The radially expandable device of claim 1, wherein the channel is configured to receive a biopsy tool therethrough.

9. The radially expandable device of claim 1, wherein the 3D tracking sensor is disposed at a distal tip of the radially expandable device.

10. The radially expandable device of claim 1, wherein the 3D tracking sensor provides tracking data pertaining to a location of the distal portion of the radially expandable device within an airway of a patient.

11. The radially expandable device of claim 1, wherein the endoscope is a bronchoscope.

12. The radially expandable device of claim 1, wherein the channel transitions from the radially expanded configuration to the unexpanded configuration along its entire length as the tool traverses the channel during removal of the tool from the channel.

13. The radially expandable device of claim 1, wherein the 3D tracking sensor is configured to assist in navigation of the distal portion of the radially expandable device to a target location within an airway of a patient.

14. The radially expandable device of claim 1, wherein the radially expandable device is configured to remain within an airway of a patient when an endoscope, through which the radially expandable device is inserted, is removed from the airway of the patient.

15. A method of accessing a target location within a patient comprising:
navigating an endoscope toward the target location;
advancing a radially expandable device through a working channel of the endoscope, the radially expandable device including a location mechanism and a flexible sheath defining a channel therein, wherein the channel is deformable along its entire length, from an unexpanded configuration to a radially expanded configuration, such that when a tool is inserted through the channel, the channel transitions from the unexpanded configuration to the radially expanded configuration along its entire length as the tool traverses the channel, the location mechanism including a three dimensional (3D) tracking sensor that provides tracking data in six degrees of freedom disposed at a distal portion of the radially expandable device, the 3D tracking sensor connected to wires leading from the 3D tracking sensor to a proximal end of the radially expandable device, the wires utilized to carry a signal from the 3D tracking sensor, and to deflect a distal end of the radially expandable device when at least one of the wires is actuated;
withdrawing the endoscope from the patient over the radially expandable device; and
passing the tool through the channel to the target location.

16. The method of claim 15, wherein the endoscope is a bronchoscope.

17. The method of claim 15, wherein advancing the radially expandable device through the working channel of the endoscope includes using the location mechanism to assist in navigating the radially expandable device to the target location.

18. The method of claim 15, including further comprising:
actuating the wires to position the distal portion of the radially expandable device adjacent the target location.

19. A method of accessing a target location within a patient comprising:
introducing a radially expandable device into a patient through a working channel of an endoscope, the radially expandable device including a location mechanism and a flexible sheath defining a channel therein, wherein the channel is deformable along its entire length, from an unexpanded configuration to a radially expanded configuration, such that when a tool is inserted through the channel, the channel transitions from the unexpanded configuration to the radially expanded configuration along its entire length as the tool traverses the channel, the location mechanism including a three dimensional (3D) tracking sensor that provides tracking data in six degrees of freedom disposed at a distal portion of the radially expandable device, the 3D tracking sensor connected to wires leading from the 3D tracking sensor to a proximal end of the radially expandable device, the wires utilized to carry a signal from the 3D tracking sensor, and to deflect a distal end of the radially expandable device when at least one of the wires is actuated;
using the location mechanism to navigate the radially expandable device to the target location; and
passing the tool through the channel to the target location, wherein the sensor and the wires are within a wall of the flexible sheath.

20. The method of claim 19, further comprising:
actuating the wires to position the distal portion of the radially expandable device adjacent the target location.

* * * * *